US011007323B2

(12) United States Patent
Schader et al.

(10) Patent No.: US 11,007,323 B2
(45) Date of Patent: May 18, 2021

(54) MEDICAMENT INJECTION DEVICE WITH PIVOTING NEEDLE HOLDER

(71) Applicant: Sanofi-Aventis Deutschland GMBH, Frankfurt am Main (DE)

(72) Inventors: Marc Schader, Frankfurt am Main (DE); Michael Helmer, Frankfurt am Main (DE); Peter Nober, Rommersheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 27 days.

(21) Appl. No.: 15/778,252

(22) PCT Filed: Nov. 21, 2016

(86) PCT No.: PCT/EP2016/078282
§ 371 (c)(1),
(2) Date: May 23, 2018

(87) PCT Pub. No.: WO2017/089290
PCT Pub. Date: Jun. 1, 2017

(65) Prior Publication Data
US 2018/0361069 A1    Dec. 20, 2018

(30) Foreign Application Priority Data

Nov. 27, 2015 (EP) .................... 15196700

(51) Int. Cl.
*A61M 5/24* (2006.01)
*A61M 5/32* (2006.01)

(52) U.S. Cl.
CPC ............ *A61M 5/24* (2013.01); *A61M 5/3202* (2013.01); *A61M 5/329* (2013.01);
(Continued)

(58) Field of Classification Search
CPC .... A61M 5/24; A61M 5/2455; A61M 5/2459; A61M 5/2466; A61M 5/3202;
(Continued)

(56) References Cited

U.S. PATENT DOCUMENTS 4,378,015 A * 3/1983 Wardlaw ............. A61M 5/2033
604/137
2012/0179110 A1    7/2012 Gratwohl et al.
(Continued)

FOREIGN PATENT DOCUMENTS

CN    101563124    10/2009
EP    2944340    11/2015
(Continued)

OTHER PUBLICATIONS

International Search Report and Written Opinion in International Application No. PCT/EP2016/078282, dated Feb. 13, 2017, 9 pages.
(Continued)

*Primary Examiner* — Shefali D Patel
(74) *Attorney, Agent, or Firm* — Fish & Richardson P.C.

(57) ABSTRACT

The present disclosure relates to a medicament injection device comprising a housing, a cartridge holder mounted in the housing and configured to receive a cartridge containing a medicament, an injection needle having a proximal end and a distal end, an injection needle holder to which the injection needle is fixed. The medicament injection device comprises an actuating mechanism for pivoting the injection needle holder relative to the cartridge holder between a storage position in which, when the cartridge is received in the cartridge holder, the distal end of the injection needle is spaced from the cartridge, and a use position in which, when the cartridge is received in the cartridge holder, the distal end of the injection needle can engage the cartridge.

15 Claims, 11 Drawing Sheets

(52) U.S. Cl.
CPC ......... *A61M 5/3293* (2013.01); *A61M 5/3257* (2013.01); *A61M 2005/2474* (2013.01)

(58) Field of Classification Search
CPC .... A61M 5/329; A61M 5/3293; A61M 5/347; A61M 2005/2474; A61M 2005/341; A61M 2005/342
See application file for complete search history.

(56) References Cited

U.S. PATENT DOCUMENTS

2013/0131589 A1   5/2013   Mudd et al.
2015/0073382 A1   3/2015   Botich

FOREIGN PATENT DOCUMENTS

JP       2000024106       1/2000
WO    WO 2015140262     9/2015

OTHER PUBLICATIONS

International Preliminary Report on Patentability in International Application No. PCT/EP2016/078282, dated May 29, 2018, 7 pages.

\* cited by examiner

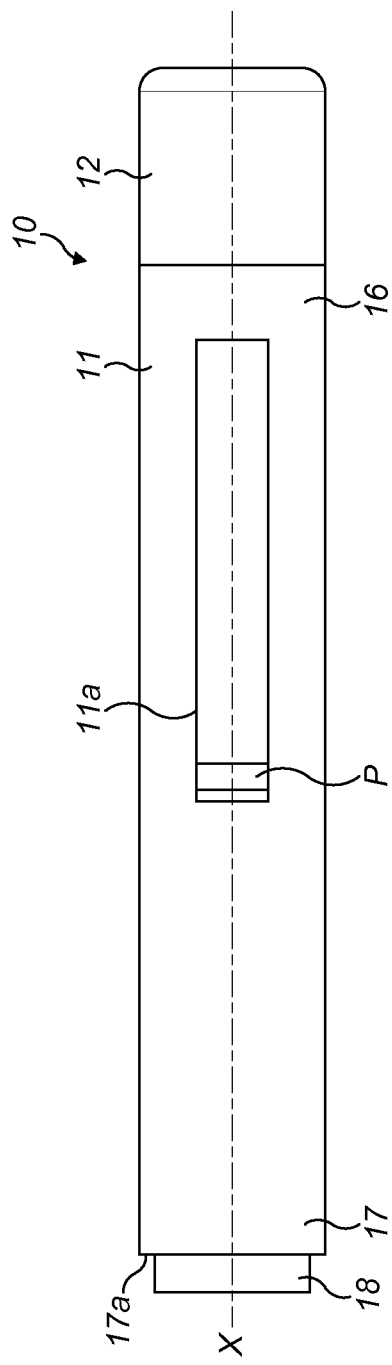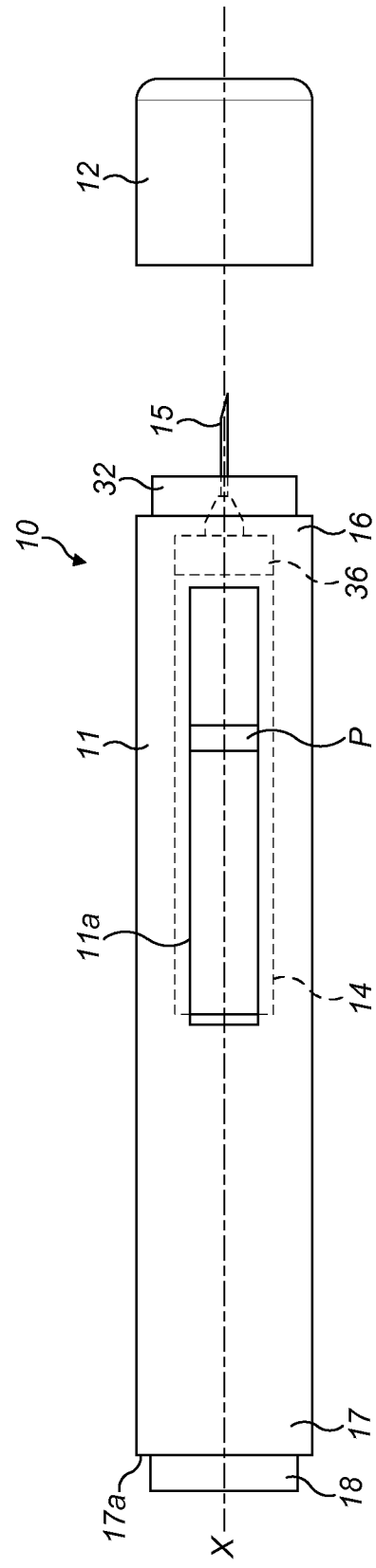
FIG. 1A
FIG. 1B

MEDICAMENT INJECTION DEVICE WITH PIVOTING NEEDLE HOLDER

CROSS REFERENCE TO RELATED APPLICATIONS

The present application is the national stage entry of International Patent Application No. PCT/EP2016/078282, filed on Nov. 21, 2016, and claims priority to Application No. EP 15196700.7, filed in on Nov. 27, 2015, the disclosures of which are incorporated herein by reference.

TECHNICAL FIELD

The present disclosure relates to a device for injection of medicament to a patient.

BACKGROUND DISCLOSURE

Auto-injectors are a common type of medicament delivery device designed to deliver a medicament by injection. Auto-injector devices are designed to be easy to use and intended for self-administration by patients, or administration by persons having no formal medical training.

Some auto-injectors operate with a cartridge-based injection system. This type of auto-injectors is typically provided with a separate cartridge pre-filled with medicament and a separate needle sealed in a sterilised packaging. Before the injection, the patient has to place the cartridge in a cartridge holder located within the housing of the auto-injector, unseal the packaging containing the needle, and position the needle in the housing of the auto-injector. Therefore, the patient has to perform several steps before being able to carry out the injection, which can be time-consuming and uncomfortable, in particular for patients of impaired physical ability.

Auto-injectors operating with a syringe-based injection system also exist. This type of auto-injectors typically comprises a syringe pre-filled with medicament having a needle already fixed to the body of the syringe. Before the injection, the patient places the syringe in the housing of the auto-injector. During the injection, the whole syringe is moved forward to penetrate the patient's skin. The syringes used with this latter type of auto-injectors are often stored during a relatively long time before being effectively used for injection. One problem is that, during this time of storage, the medicament remains in contact with the needle of the syringe and a clogging of the needle by the medicament may occur. This may delay the delivery of medicament during the injection and therefore increase the injection time.

At least in certain embodiments, the present disclosure sets out to overcome or ameliorate at least some of the problems mentioned above. In particular, the present disclosure sets out to provide a device for injection of medicament of convenient and efficient use.

SUMMARY OF THE DISCLOSURE

Aspects of the present disclosure relate to a device for injection of medicament to a patient.

According to a further aspect of the present disclosure, there is provided a medicament injection device comprising:
a housing,
a cartridge holder mounted in the housing and configured to receive a cartridge containing a medicament,
an injection needle having a proximal end and a distal end,
an injection needle holder to which the injection needle is fixed, and
an actuating mechanism for pivoting the injection needle holder relative to the cartridge holder between a storage position in which, when a cartridge is received in the cartridge holder, the distal end of the injection needle is spaced from the cartridge, and a use position in which, when a cartridge is received in the cartridge holder, the distal end of the injection needle can engage the cartridge. This may advantageously reduce the number of steps required before performing the injection, such as unsealing the injection needle from a separate packaging, and positioning the injection needle in the housing of the medicament delivery device. This may also advantageously avoid that the distal end of the injection needle remains in contact with the medicament during a long time prior injection and that the injection needle gets clogged by the medicament.

The injection needle holder may be pivotally mounted to the cartridge holder. This may advantageously allow the needle to pivot in a compact device configuration.

The medicament injection device may comprise a locking mechanism adapted to hold the injection needle in the use position. This may advantageously ensure that the injection needle is secured in the use position during injection.

The locking mechanism may include a first locking element provided on the cartridge holder and a second locking element provided on the injection needle holder. When the injection needle holder is in the use position, the first and second locking elements may cooperate to prevent the injection needle from moving towards the storage position. This may advantageously provide a locking feature for the injection needle in the use position in a compact device configuration.

The medicament injection device may comprise a retaining mechanism to retain the injection needle in the storage position. This may advantageously prevent the injection needle from moving in the housing when the device is not in use.

The injection needle may comprise a curved region between the distal end and the proximal end. This may advantageously facilitates the insertion of the distal end of the needle in the cartridge when the needle moves towards the use position.

The medicament injection device may comprise a cap for shielding the proximal end of the injection needle, the cap being detachably mounted to the housing. This may advantageously provide a safety feature to protect the user from exposure to the proximal end of the needle when the device is not in use.

The actuating mechanism may be configured such that pulling the cap away from the housing causes the injection needle to pivot from the storage position towards the use position. This may advantageously allow rotation of the injection needle towards the use position while the cap is removed from the housing, without requiring further action from a user.

The actuating mechanism may comprise a first projection provided on the injection needle holder and a second projection provided on the cap, the first and second projections being configured such that pulling the cap away from the housing causes engagement of the second projection with the first projection and consequent pivotal movement of the injection needle holder from the storage position towards the use position. This may advantageously provide an efficient actuating mechanism in a compact device configuration.

The actuating mechanism may comprise a gear provided on the injection needle holder and a plurality of teeth disposed on the cap, the gear and the plurality of teeth cooperating so that pulling the cap away from the housing causes rotational movement of the gear and consequent pivotal movement of the injection needle holder from the storage position towards the use position. This may advantageously provide an alternative configuration of device to be produced.

The actuating mechanism may comprise an actuator protruding through a sidewall of the housing and connected to the injection needle holder. Moving the actuator relative to the housing may cause pivotal movement of the injection needle holder between the storage position and the use position. This may advantageously allow the user to actuate the actuating mechanism from outside the device while holding the device in his hand.

The actuator may comprise a plurality of teeth and the injection needle holder may comprise a gear. The gear and the plurality of teeth may be configured to cooperate so that sliding the actuator relative to the housing causes rotational movement of the gear and consequent pivotal movement of the injection needle holder from the storage position towards the use position. This may advantageously provide a further alternative configuration of device to be produced.

The actuator may comprise an arm integrally formed with the injection needle holder. This may advantageously provide a device which is simple to produce.

The medicament injection device may comprise a retractable sleeve mounted in the housing and configured to slide along a longitudinal axis of the housing between a deployed position in which the sleeve protrudes from the housing and a retracted position in which the sleeve is retracted within the housing. This may advantageously provide a safety feature to protect the user from exposure to the proximal end of the needle.

The actuating mechanism may be configured such that pushing the sleeve towards the cartridge holder causes the injection needle holder to move from the storage position towards the use position. This may advantageously allow rotation of the injection needle towards the use position while the sleeve retracts within the housing, without requiring further action from a user.

The sleeve may comprise a lug configured to engage an end of the injection needle holder when the sleeve is pushed towards the retracted position such that the injection needle holder pivots from the storage position towards the use position. This may advantageously provide an efficient actuating mechanism in a compact device configuration.

The medicament injection device may comprise a cartridge of medicament, the cartridge being received in the cartridge holder. This may advantageously reduce the amount of steps a user must perform for a medicament injection procedure.

The medicament injection device may be an auto-injector.

BRIEF DESCRIPTION OF THE FIGURES

Embodiments of the present disclosure will now be described, by way of example only, with reference to the accompanying Figures, in which:

FIGS. 1A and 1B show schematic side views of a medicament injection device which may include embodiments of the present disclosure;

DETAILED DESCRIPTION

Figure 2A:
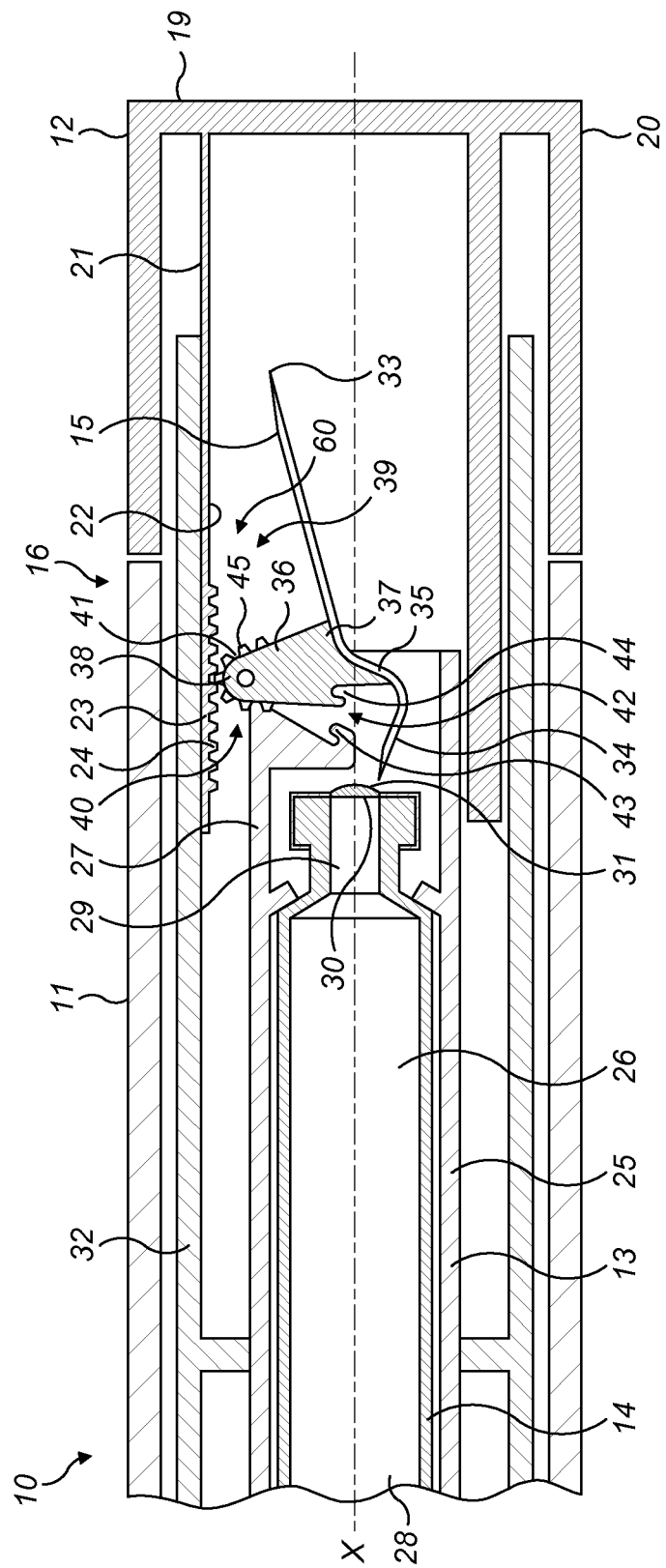
FIG. 2A shows a cross-sectional view of a part of a medicament injection device according to a first embodiment of the present disclosure, the injection needle being in a storage position.

Embodiments of the disclosure provide a mechanism for inserting the injection needle of a medicament injection device such as an auto-injector into a medicament cartridge containing the medicament to be injected. Providing such a mechanism allows the medicament cartridge to be sealed until such time as the user wishes to commence the injection. Providing an automated mechanism for inserting the needle into the medicament cartridge also reduces the amount of handling of the needle by the user prior to the injection. Indeed, in embodiments of the disclosure, the user does not need to touch the needle during the steps of inserting the needle into the medicament cartridge and subsequently actuating the injection of the medicament.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap or cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a proximal region 16 and a distal region 17. The term "proximal" refers to a location that is relatively closer to a site of injection, and the term "distal" refers to a location that is relatively further away from the injection site.

Device 10 can also include a needle sleeve 32 coupled to housing 11 to permit movement of sleeve 32 relative to housing 11. For example, sleeve 32 can move in a longitudinal direction parallel to longitudinal axis X. Specifically, movement of sleeve 32 in a distal direction can permit a needle 15 to extend from proximal region 16 of housing 11.

Insertion of needle 15 can occur via several mechanisms. For example, needle 15 may be fixedly located relative to housing 11 and initially be located within an extended needle sleeve 32. Distal movement of sleeve 32 by placing a proximal end of sleeve 32 against a patient's body and moving housing 11 in a proximal direction will uncover the proximal end of needle 15. Such relative movement allows the proximal end of needle 15 to extend into the patient's body. Such insertion is termed "manual" insertion as needle 15 is manually inserted via the patient's manual movement of housing 11 relative to sleeve 32.

Another form of insertion is "automated," whereby needle 15 moves relative to housing 11. Such insertion can be triggered by movement of sleeve 32 or by another form of activation, such as, for example, a button 18. As shown in FIGS. 1A & 1B, button 18 is located at a distal end 17a of housing 11. However, in other embodiments, button 18 could be located on a side of housing 11.

Other manual or automated features can include drug injection or needle retraction, or both. Injection is the process by which a bung or piston P is moved from a distal location within a syringe (not shown) to a more proximal location within the syringe in order to force a medicament from the syringe through needle 15. In some embodiments, a drive spring (not shown) is under compression before device 10 is activated. A distal end of the drive spring can be fixed within distal region 17 of housing 11, and a proximal end 16 of the drive spring can be configured to apply a compressive force to a distal surface of piston P. Following activation, at least part of the energy stored in the drive spring can be applied to the distal surface of piston P. This compressive force can act on piston P to move it in a proximal direction. Such proximal movement acts to compress the liquid medicament within the syringe, forcing it out of needle 15.

Following injection, needle 15 can be retracted within sleeve 32 or housing 11. Retraction can occur when sleeve 32 moves proximally as a user removes device 10 from a patient's body. This can occur as needle 15 remains fixedly located relative to housing 11. Once a proximal end of sleeve 32 has moved past a proximal end of needle 15, and needle 15 is covered, sleeve 32 can be locked. Such locking can include locking any distal movement of sleeve 32 relative to housing 11.

Another form of needle retraction can occur if needle 15 is moved relative to housing 11. Such movement can occur if the syringe within housing 11 is moved in a distal direction relative to housing 11. This distal movement can be achieved by using a retraction spring (not shown), located in proximal region 16. A compressed retraction spring, when activated, can supply sufficient force to the syringe to move it in a distal direction. Following sufficient retraction, any relative movement between needle 15 and housing 11 can be locked with a locking mechanism. In addition, button 18 or other components of device 10 can be locked as required.

The device 10 according to the present disclosure comprises a cartridge holder 13 which receives a cartridge 14 pre-filled with medicament. As visible in FIGS. 1A and 1B, a window 11a is provided on the housing 11 so that the quantity of medicament remaining in the cartridge 14 is visible from outside the device 10.

As shown in FIG. 2A, the cap 12 is detachably mounted to the proximal region 16 of the housing 11. When the cap 12 is mounted to the proximal region 16, the cap 12 shields the needle 15 to protect the patient from premature exposure to the needle 15. Rotation of the cap 12 relative to the housing 11 is prevented by a splined engagement (not shown). The cap 12 comprises a cap surface 19 from which extend an outer cap portion 20 and an inner cap portion 21.

The outer cap portion 20 and the inner cap portion 21 protrude substantially perpendicularly from the cap surface 19. When the cap 12 is mounted to the proximal region 16, the cap surface 19 is substantially perpendicular to the longitudinal axis X and the outer and inner cap portions 20, 21 extend substantially parallel to the longitudinal axis X of the housing 11. The outer cap portion 20 and the inner cap portion 21 are cylindrical and concentric to each other. The outer cap portion 20 has a diameter which substantially equals the diameter of the housing 11. The inner cap portion 21 has a diameter which is less than the diameter of the housing 11 such that the inner cap portion 21 is partially inserted in the proximal region 16 when the cap 12 is mounted to proximal region 16. The inner cap portion 21 has an inner sidewall 22 which comprises a row 23 of teeth 24 arranged linearly along the inner sidewall 22. The row 23 of teeth 24 extends substantially parallel to the longitudinal axis X when the cap 12 is mounted to the proximal region 16. The row 23 of teeth 24 is positioned on the inner sidewall 22 such that when the cap 12 is mounted to the housing 11, the row 23 of teeth 24 is located within the housing 11.

The cartridge holder 13 is substantially cylindrical and has a substantially constant diameter along the longitudinal axis X. The cartridge holder 13 is mounted to the housing 11. The cartridge holder 13 comprises a main portion 25 defining a cavity 26 for receiving the cartridge 14, and a proximal portion 27 extending beyond the cavity 26. When the cap 12 is mounted to the housing 11, the proximal portion 27 of the cartridge holder 13 faces the row 23 of teeth 24 of the inner cap portion 24.

The cartridge 14 is in the form of a substantially cylindrical container 28 which stores the liquid medicament to be injected to the patient's body. The container 28 is fitted securely within the cartridge holder 13. The container 28 includes an end portion 29 having a transverse aperture 30 sealed by means of a septum 31. The end portion 29 locates in the proximal portion 27 of the cartridge holder 14.

Figure 2B:
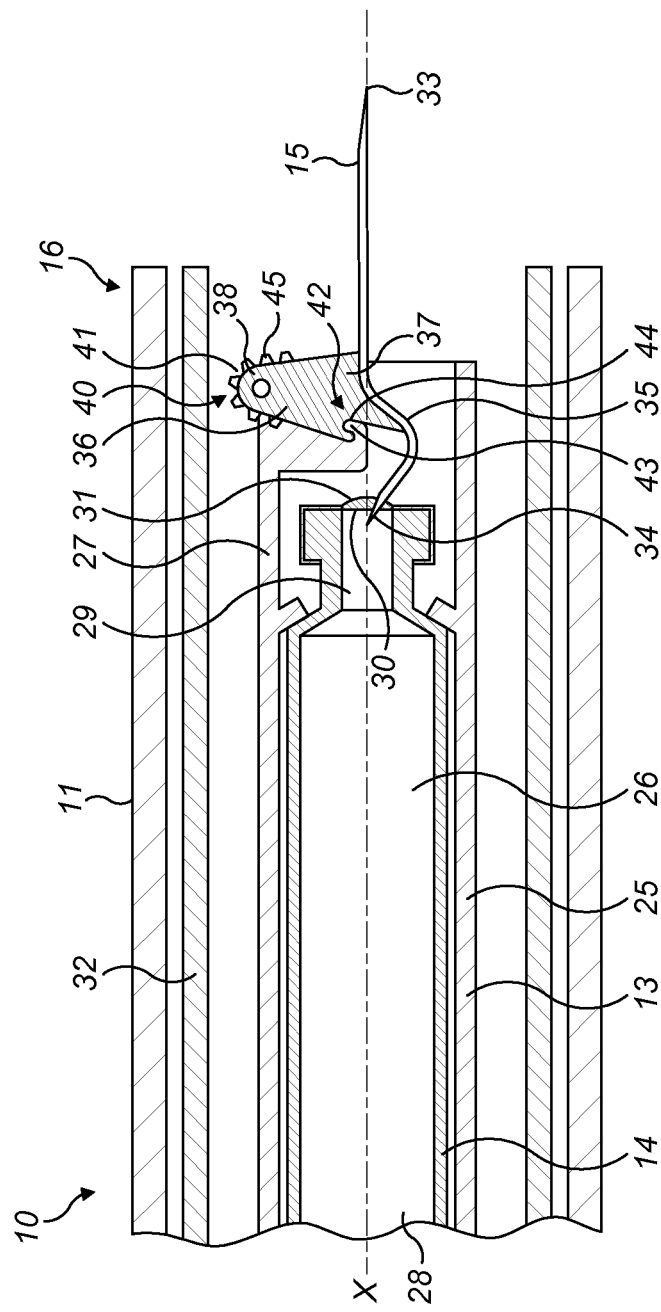
FIG. 2B shows a cross-sectional view of a part of the medicament injection device according to the first embodiment, the injection needle being in a use position.

The sleeve 32 is retractably mounted in the housing 11. The sleeve 32 has a generally annular shape and extends along the longitudinal axis X, between the housing 11 and the cartridge holder 13. The sleeve 32 is slidable along the longitudinal axis X between a deployed position in which the sleeve 32 protrudes from the proximal region 16 of the housing 11 (FIG. 2A) and a retracted position in which the sleeve 32 is retracted within the housing 11 (FIG. 2B). Rotation of the sleeve 32 relative to the housing 11 is prevented by a splined engagement (not shown).

The needle 15 comprises a proximal end 33, a distal end 34, and an intermediate section 35 joining the proximal end 33 and the distal end 34 together. The intermediate section 35 is curved in such a way that the proximal end 33 and the distal end 34 each extend along different directions. The needle 15 is pivotally mounted to the proximal portion 27 of the cartridge holder 13 by means of a needle holder 36. The needle holder 36 comprises a first end 37 and a second end 38. The first end 37 is fixed to the intermediate section 35 of the needle 15. The second end 38 is pivotally mounted to the proximal portion 27 of the cartridge holder 13, such that the needle 15 is pivotable relative to the cartridge holder 13 by means of the needle holder 36. The needle 15 is pivotable between a storage position and a use position. In the storage position, the distal end 34 of the needle 15 is spaced from the cartridge 14 such that the needle 15 cannot engage the cartridge 14. In the use position, the distal end 34 of the needle 15 is inserted in the cartridge 14. When the needle 15 is in the use position, the proximal end 33 of the needle 15 is aligned with the longitudinal axis X whereas the distal end 34 of the needle 15 extends obliquely relative to the longitudinal axis X and the aperture 30 of the cartridge 14 (as visible in FIG. 2B).

The device 10 comprises an actuating mechanism 39 for pivoting the needle 15 between the storage position and the use position. In the present embodiment, the actuating mechanism 39 comprises the row 23 of teeth 24 of the cap 12 and a gear section 40 comprising a plurality of teeth 45 and located along an edge 41 of the second end 38 of the needle holder 36. The gear section 40 faces the row 23 of teeth 24 in such a way that when the cap 12 is pulled away from the housing 11, the teeth 24 of the row 23 engages the teeth 45 of the gear section 40 so that the gear section 40 rotates and the injection needle 15 pivots from the storage position towards the use position. When the cap 12 is mounted to the proximal region 16, the row 23 of teeth 24 and the gear section 40 also form a retaining mechanism 60 to retain the needle 15 in the storage position.

A locking mechanism 42 is provided in the device 10 and adapted to lock the needle 15 in the use position. In the present embodiment, the locking mechanism 42 includes a first locking element in the form of a projection 43 protruding from the cartridge holder 13, and a second locking element in the form of a recess 44 formed in the needle holder 36. The projection 43 and the recess 44 are configured to cooperate to form a snap-fit connection to releasably lock the needle 15 in the use position.

Initially, the cap 12 is mounted to the housing 11 and the cartridge 14 filled with medicament is received in the cartridge holder 13. The teeth 24 of the row 23 cooperate with the teeth 45 of the gear section 40 so that the needle 15 is retained in the storage position (FIG. 2A). In use of the device 10, a user detaches the cap 12 from the proximal region 16 by pulling the cap 12 away from the housing 11. As the inner cap portion 21 slides away from the housing 11, the teeth 24 of the row 23 engage the teeth 45 of the gear section 40 to drives the needle holder 36 in rotation such that the needle 15 pivot from the storage position towards the use position. As the needle 15 pivots, the distal end 34 moves closer to the cartridge 14 until the distal end 34 pierces the septum 31 and the proximal end 33 is aligned with the longitudinal axis X. At this point, the projection 43 engages the recess 44. The needle 15 is therefore locked in the use position and the device 10 is ready for injection (FIG. 2B). To perform an injection, the sleeve 32 is retracted into the housing 11 so that the proximal end 33 projects outside the device 10. The medicament is then injected to the patient in a well-known manner. After the injection, the sleeve 32 extends again in the deployed position such that the sleeve 32 covers the proximal end 33 to protect the user from exposure to the needle 15.

Once the injection has been performed, the user places the cap 12 back on the housing 11. As the inner cap portion 21 slides in the housing 11 towards the cartridge holder 13, the teeth 24 of the row 23 engage the teeth 45 of the gear section 40 to drive the needle holder 36 in rotation such that the needle 15 pivots back towards the storage position.

Figure 3A:
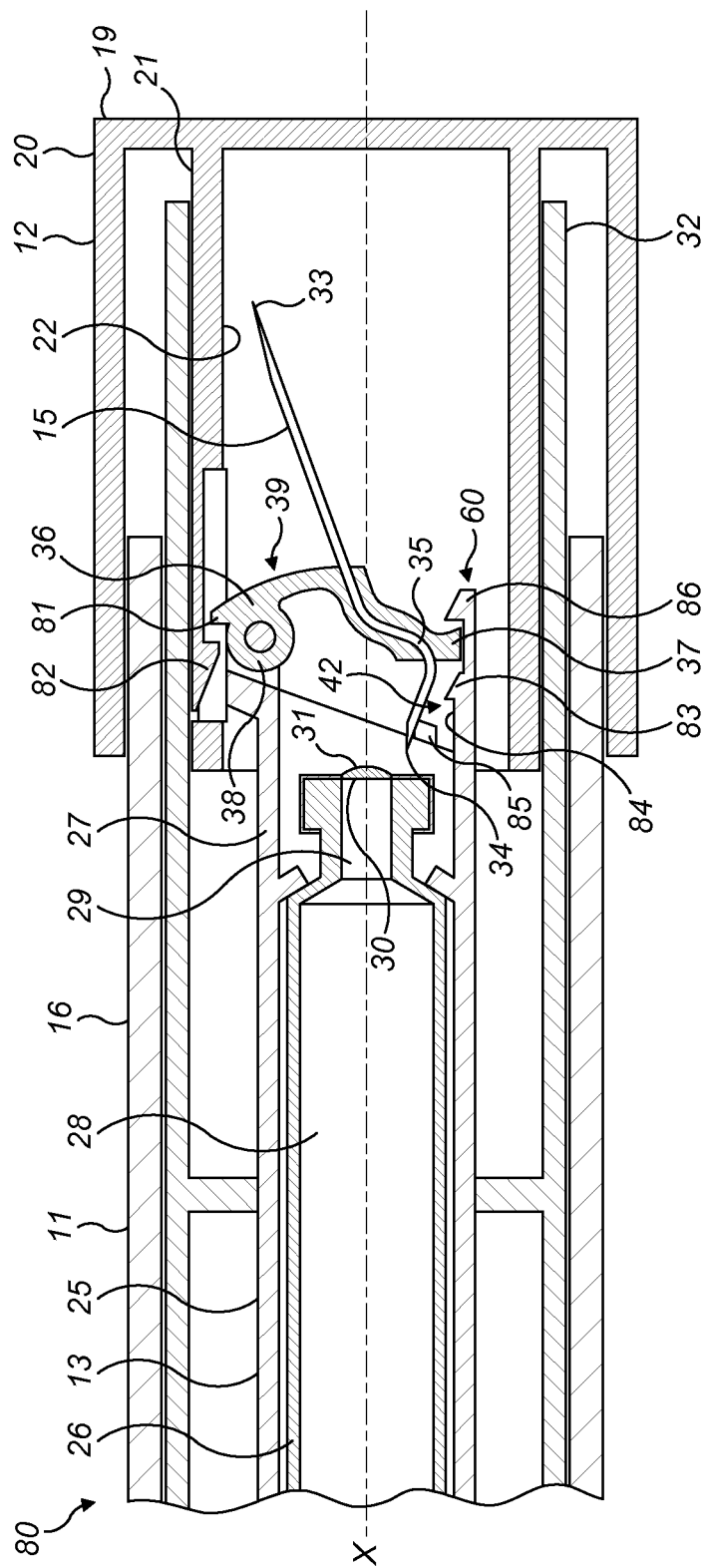
FIG. 3A shows a cross-sectional view of a part of a medicament injection device according to a second embodiment of the present disclosure, the injection needle being in a storage position.
Figure 3B:
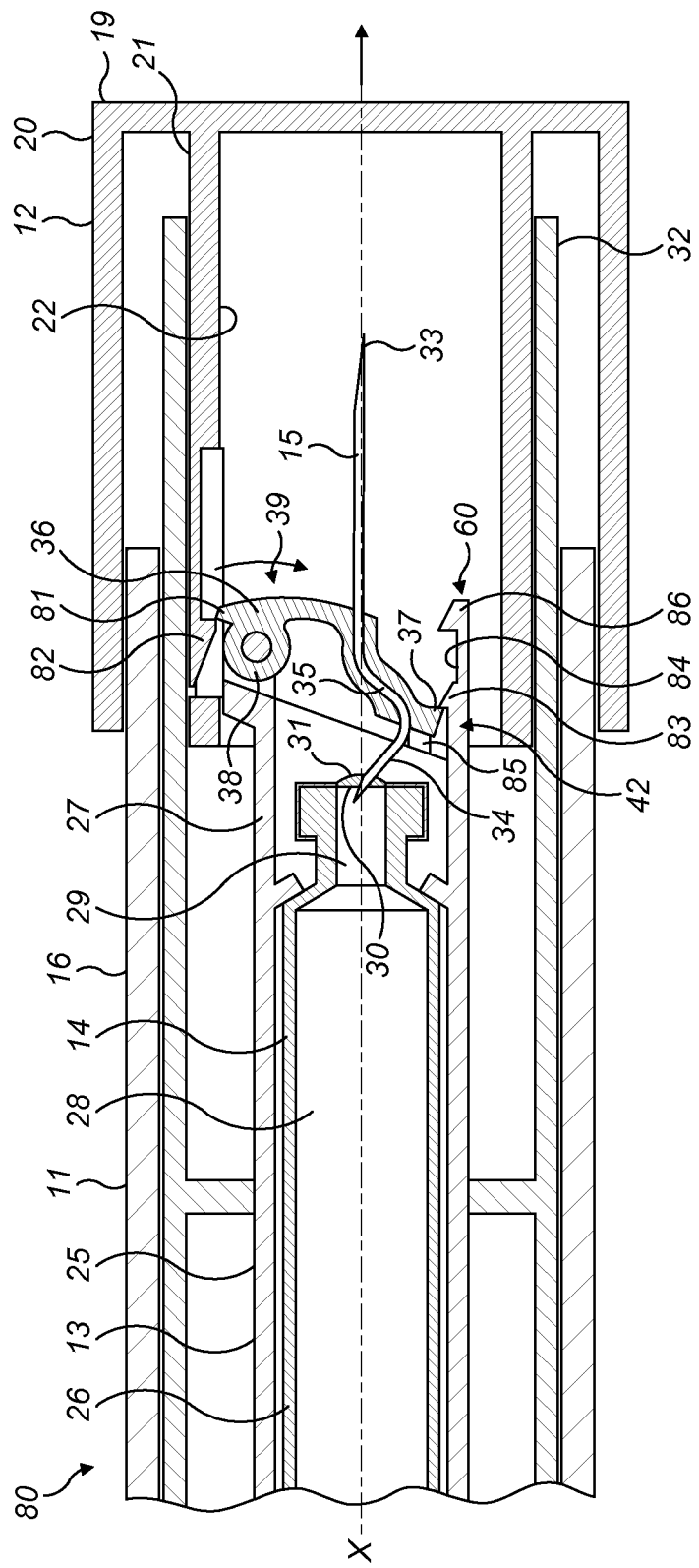
FIG. 3B shows a cross-sectional view of a part of the medicament injection device according to the second embodiment, the injection needle being in a use position.

A medicament injection device 80 according to a second embodiment of the present disclosure is shown in FIGS. 3A and 3B. The second embodiment corresponds closely to the first embodiment and like reference numerals have been used for like components. Differences in relation to the first embodiment are described below.

In the device 80, the actuating mechanism 39 comprises a first projection 81 protruding from the needle holder 36 and a second projection 82 protruding from the inner sidewall 22 of the inner cap portion 21. The second projection 82 is configured to engage the first projection 81 when the cap is pulled away from the housing such that the needle holder 36 pivots from the storage position towards the use position.

In the device 80, the locking mechanism 42 includes the first end 37 of the needle holder 36 and a hook 83 provided on an inner surface 84 of the cartridge holder 13. The first end 37 of the needle holder 36 is configured to engage the hook 83 when the needle 15 is moved towards the use position. Once the needle 15 is in the use position, the first end 37 abuts the hook 83 such that the needle 15 is prevented from moving back towards the storage position. The locking mechanism 42 also comprises a stop 85 provided on the cartridge holder 13. The stop 85 is configured to stop the course of the needle 15 once the needle 15 has reached the use position. Therefore, the hook 83 and the stop 85 are configured to cooperate with the first end 37 of the needle holder 36 to lock the needle holder 36 in the use position.

In the device 80, the retaining mechanism 60 in the form of a clip 86 protruding from the inner surface 84 of the cartridge holder 13. The clip 86 is configured to engage the first end 37 of the needle holder 36 to stop the course of the needle 15 once the needle 15 has reached the storage position.

Initially, the cap 12 is mounted to the housing 11 and the cartridge 14 filled with medicament is received in the cartridge holder 13. The clip 86 retains the needle in the storage position (FIG. 3A). In use of the device 80, a user detaches the cap 12 from the proximal region 16 by pulling the cap 12 away from the housing 11. As the inner cap portion 21 slides away from the housing 11, the second projection 82 engages the first projection 81, such that the needle holder 36 pivots from storage position towards the use position (FIG. 3B). As the needle 15 pivots, the distal end 34 of the needle 15 moves closer to the cartridge 14 until the distal end 34 pierces the septum 31 of the cartridge 14 and the first end 37 is stopped by the stop 85. Simultaneously, the first end 37 of the needle holder 36 engages the hook 83. The needle 15 is therefore locked in the use position and the device 80 is ready for injection (FIG. 3B).

Figure 4:
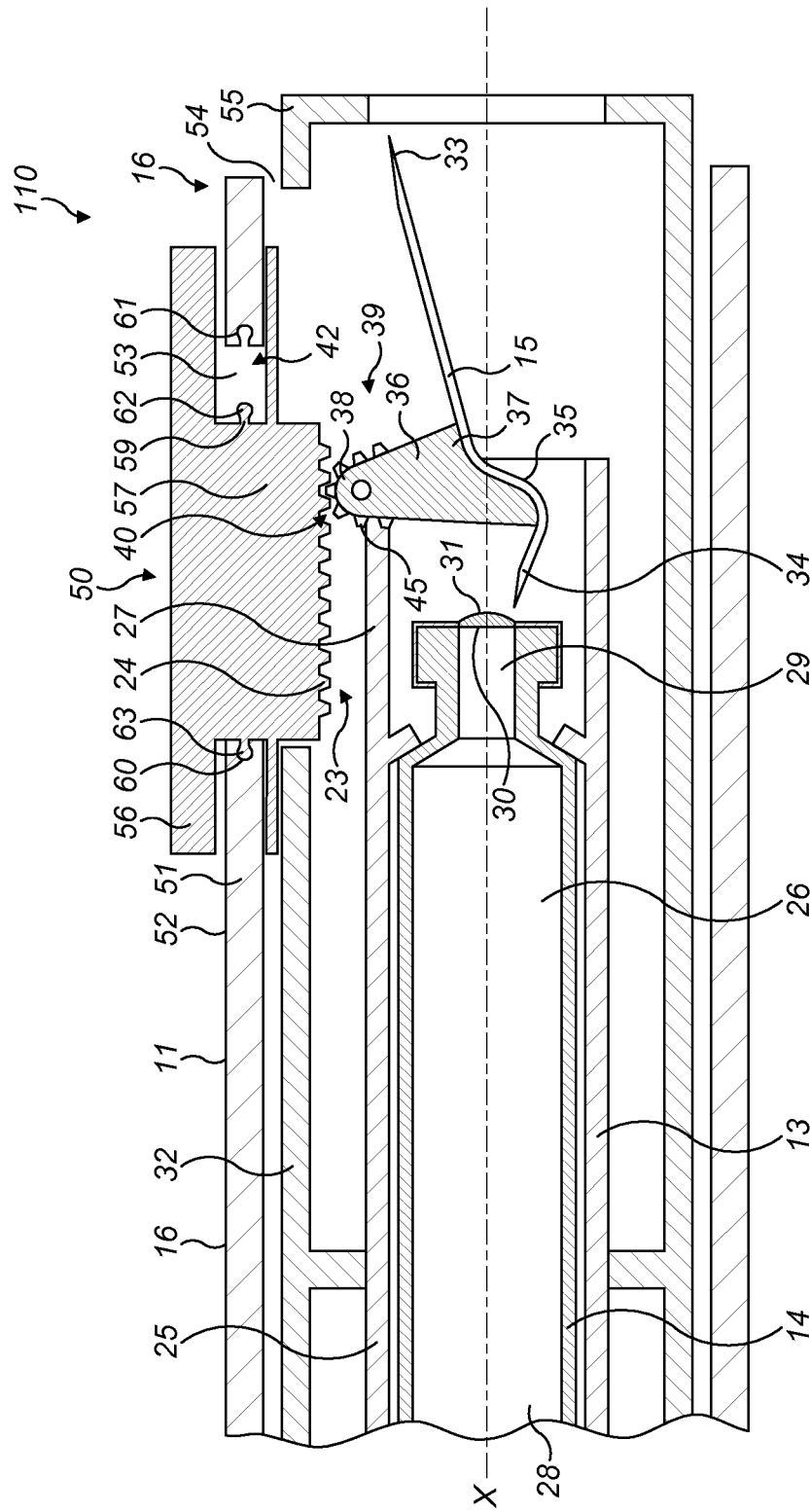
FIG. 4 shows a cross-sectional view of a part of a medicament injection device according to a third embodiment of the present disclosure, the injection needle being in a storage position.

The actuating mechanism 39 of the devices 10, 80 of the first and second embodiments of the disclosure shown in FIGS. 2A to 3B are configured such that pulling the cap 12 away from the housing 11 causes pivoting movement of the needle 15 from the storage position towards the use position. However, the disclosure is not intended to be limited to this configuration or motion, or this particular type of actuating mechanism. Accordingly, a medicament injection device 110 according to a third embodiment of the present disclosure is shown in FIG. 4 and is similar to the first embodiment, and like reference numerals have been used for like components. Differences in relation to the first embodiment are described below.

As shown in FIG. 4, the actuating mechanism 39 comprises an actuator in the form of a bar 50 slidingly mounted to the housing 11. The housing 11 comprises a sidewall 51 having an outer surface 52 and in which a first aperture 53 is formed. The sleeve 32 comprises a sidewall 55 in which a second aperture 54 is formed. The bar 50 comprises an external portion 56 lying over the outer surface 52 of the housing 11 and configured to be actuated by a user, for example by a finger of the user. The bar 50 comprises an internal portion 57 extending within the housing 11 and the sleeve 32 through the first and second apertures 53, 54. The internal portion 57 has an internal surface 58 on which linear row 23 of teeth 24 is arranged. The linear row 23 of teeth 24 extends substantially parallel to the longitudinal axis X. The bar 50 is positioned relative to the housing 11 such that the internal surface 58 of the internal portion 57 of the bar 50 faces the proximal portion 27 of the cartridge holder 13. The needle holder 36 comprises a gear section 40 having a plurality of teeth 45. The gear section 40 is located along an edge 41 of the second end 38 of the needle holder 36. The gear section 40 faces the row 23 of teeth 24 in such a way that when a user slides the bar 50 along the housing 11, the teeth 24 of the row 23 engage the teeth 45 of the gear section 40 to drive the needle holder 36 in rotation and pivot the needle from the storage position towards the use position.

In the device 110, the locking mechanism 42 comprises a locking recess 61 formed in the sidewall 51 of the housing 11 and a locking projection 62 formed on a side surface 59 of the internal portion 57 and facing the locking recess 61. The locking projection 62 and the locking recess 61 are configured to cooperate to form a snap-fit connection to releasably lock the needle 15 in the use position.

In the device 110, the retaining mechanism 60 is in the form of a snap-fit connection 63 configured to retain the internal portion 57 of the bar 50 against the sidewall 51 of the housing 11 and therefore prevent the bar 50 from sliding along the housing 11 and consequently pivoting the needle 15 towards the use position.

Initially, the connection 63 retains the internal portion 57 of the bar 50 against the housing 11 such that the needle 15 is held in the storage position. In use of the device 110, a user detaches the cap 12 from the proximal region 16 by pulling the cap 12 away from the housing 11. Then, the user slides the bar 50 along the housing 11 so that the teeth 24 of the row 23 engage the teeth 45 of the gear section 40 to drive the needle holder 36 in rotation and pivot the needle 15 from the storage position towards the use position. As the needle 15 pivots towards the use position, the locking projection 62 on the bar 50 engages the locking recess 61 in the sidewall 51 of the housing 11. The needle 15 is then locked in the use position and the device 110 is ready for injection. Once the injection has been performed, the user slides the bar 50 back towards the distal region 17. The teeth 24 of the row 23 engage the teeth 45 of the gear section 40 to drive the needle 15 back towards the storage position.

Figure 5:
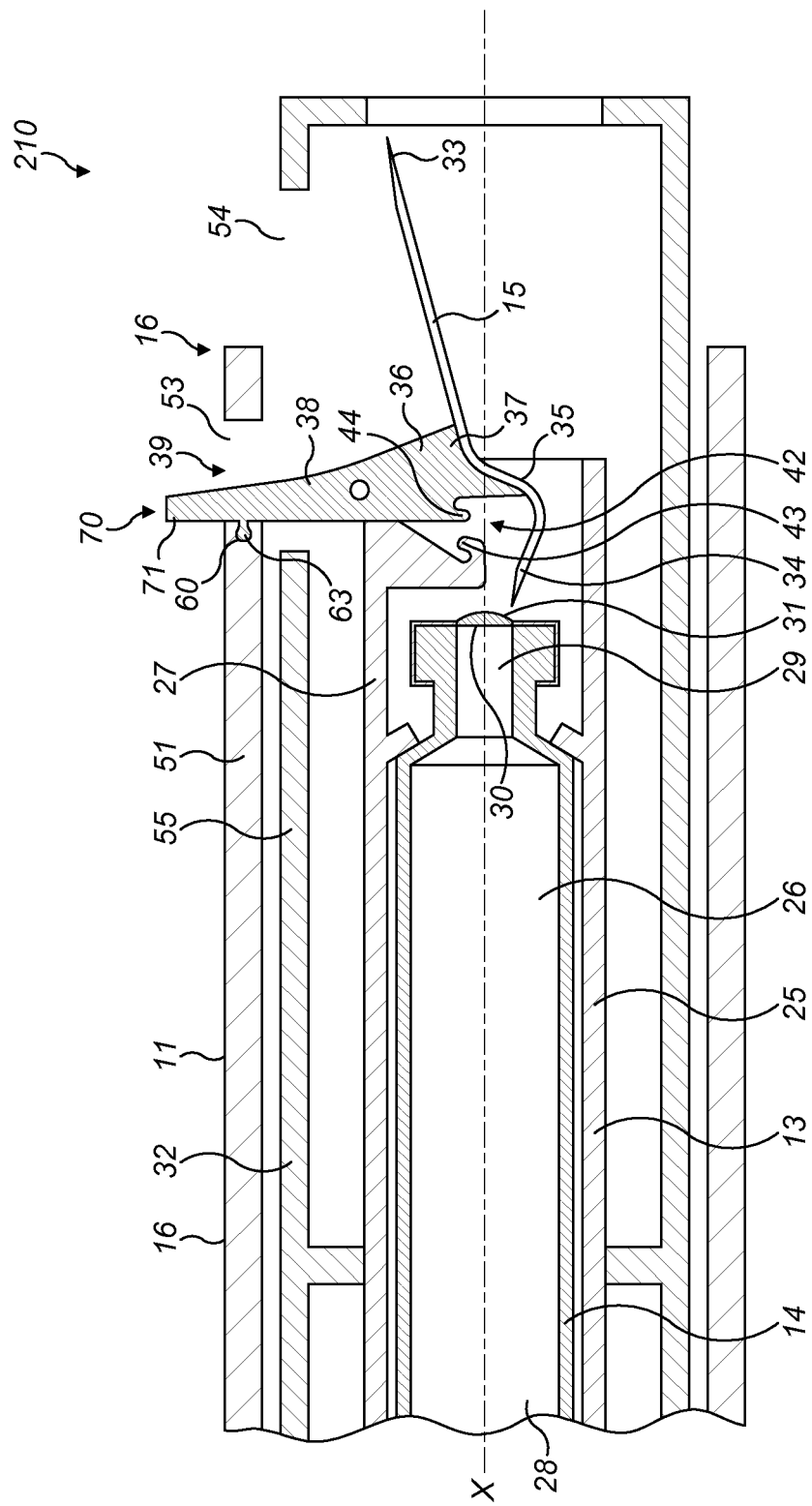
FIG. 5 shows a cross-sectional view of a part of a medicament injection device according to a fourth embodiment of the present disclosure, the injection needle being in a storage position.

A medicament injection device 210 according to a fourth embodiment of the present disclosure is shown in FIG. 5. The fourth embodiment corresponds closely to the first embodiment and like reference numerals have been used for like components. Differences in relation to the first embodiment are described below.

As shown in FIG. 5, the actuating mechanism 39 comprises an actuator in the form of an arm 70 integrally formed with the needle holder 36. The housing 11 comprises a sidewall 51 in which a first aperture 53 is formed. The sleeve 32 comprises a sidewall 55 in which a second aperture 54 is formed. The arm 70 extends from the needle holder 36 through the first and second apertures 53, 54 such that an end 71 of the arm 70 protrudes outside of the housing 11. The end 71 of the arm 70 is configured to be actuated by a user to pivot the needle 15 between the storage position and the use position. In the device 210, the locking mechanism 42 is similar to the locking mechanism of the device 10 according to the first embodiment of the disclosure.

In the device 210, the retaining mechanism 60 is in the form of a snap-fit connection 63 configured to retain the arm 70 against the sidewall 51 of the housing 11 and therefore prevent the arm 70 from pivoting relative to the housing 11 and consequently pivoting the needle 15 towards the use position.

A medicament injection device 310 according to a fifth embodiment of the present disclosure is shown in FIGS. 6A to 6D. The fifth embodiment corresponds closely to the first embodiment and like reference numerals have been used for like components. Differences in relation to the first embodiment are described below.

In the device 310, the actuating mechanism 39 is configured such that pushing the sleeve 32 towards the cartridge holder 13 causes the injection needle holder 36 to move from the storage position towards the use position. As shown in FIG. 5, the sleeve 32 is provided with a lug 73 protruding in a slot 75 formed the sleeve 32. The lug 73 is configured to engage the first end 37 of the needle holder 36 when the sleeve 32 is pushed towards the retracted position such that the needle holder 36 pivots from the storage position towards the use position. The lug 73 is resilient such that the lug 73 is deflectable. In the device 310, the locking mechanism 42 includes an opening 74 formed in the needle holder 36 and a hook 76 protruding from the cartridge holder 13. In the use position, the hook 76 is received in the opening 74 and engages the needle holder 36 such that the needle 15 is prevented from moving back towards the storage position. The locking mechanism 42 also comprises a stop 77 provided on the cartridge holder 13. The stop 77 is configured to stop the course of the needle 15 once the needle 15 has reached the use position. Therefore, the hook 76 and the stop 77 are configured to cooperate with the needle holder 36 to hold the needle holder 36 in the use position.

Figure 6A:
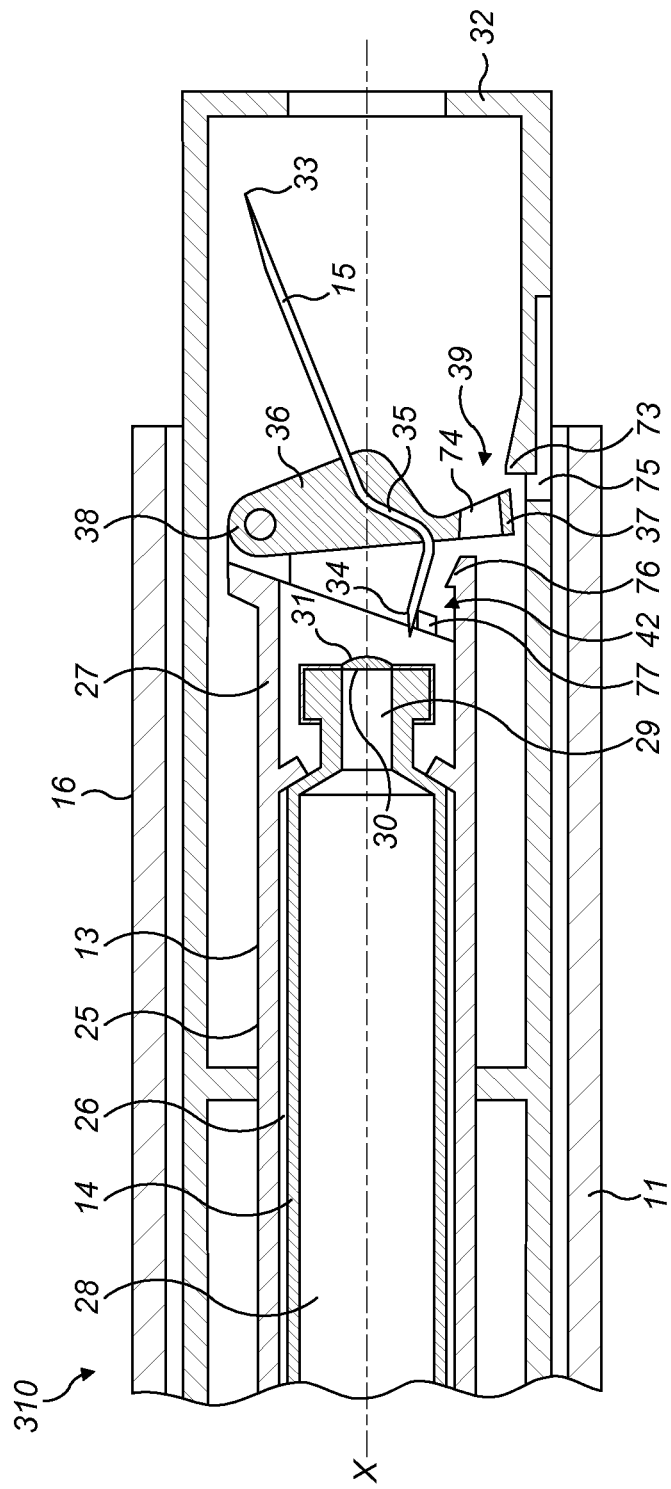
FIGS. 6A to 6D show cross-sectional views of a part of a medicament injection device according to a fifth embodiment of the present disclosure.
Figure 6B:
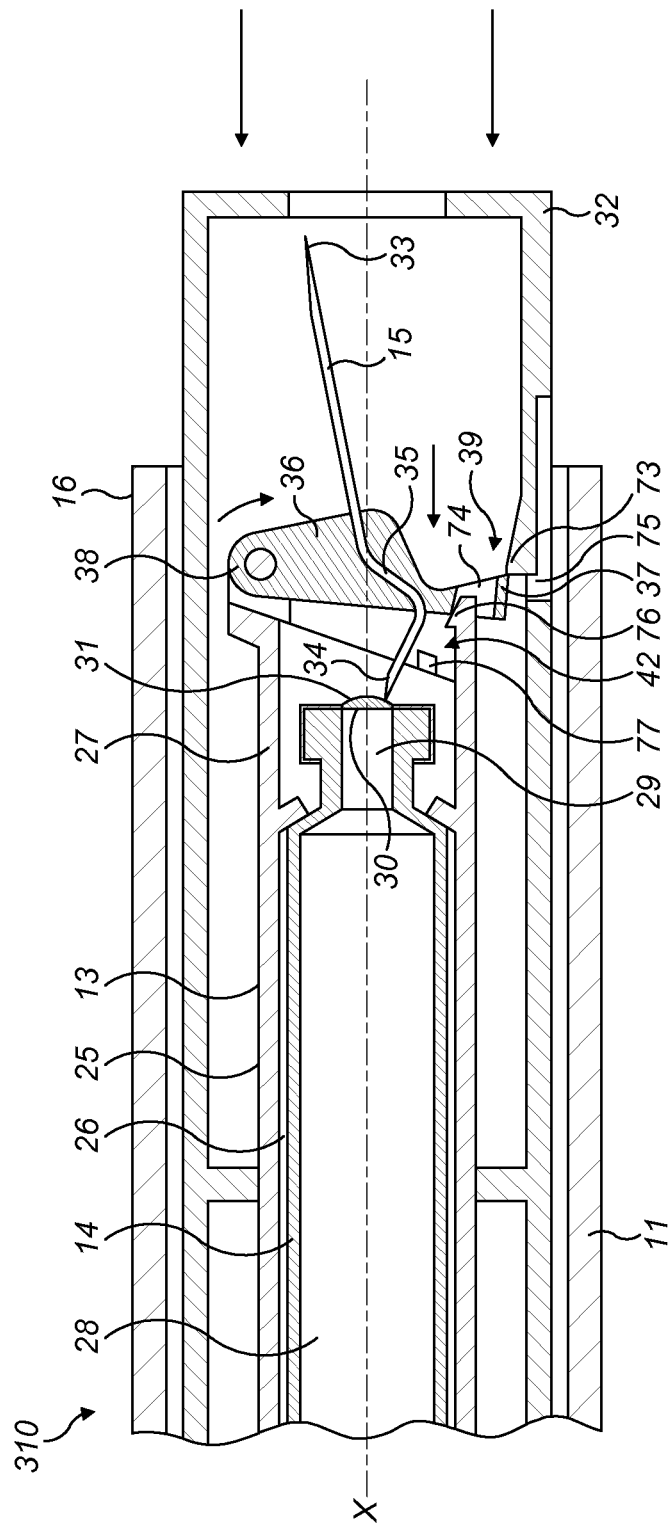
Figure 6C:
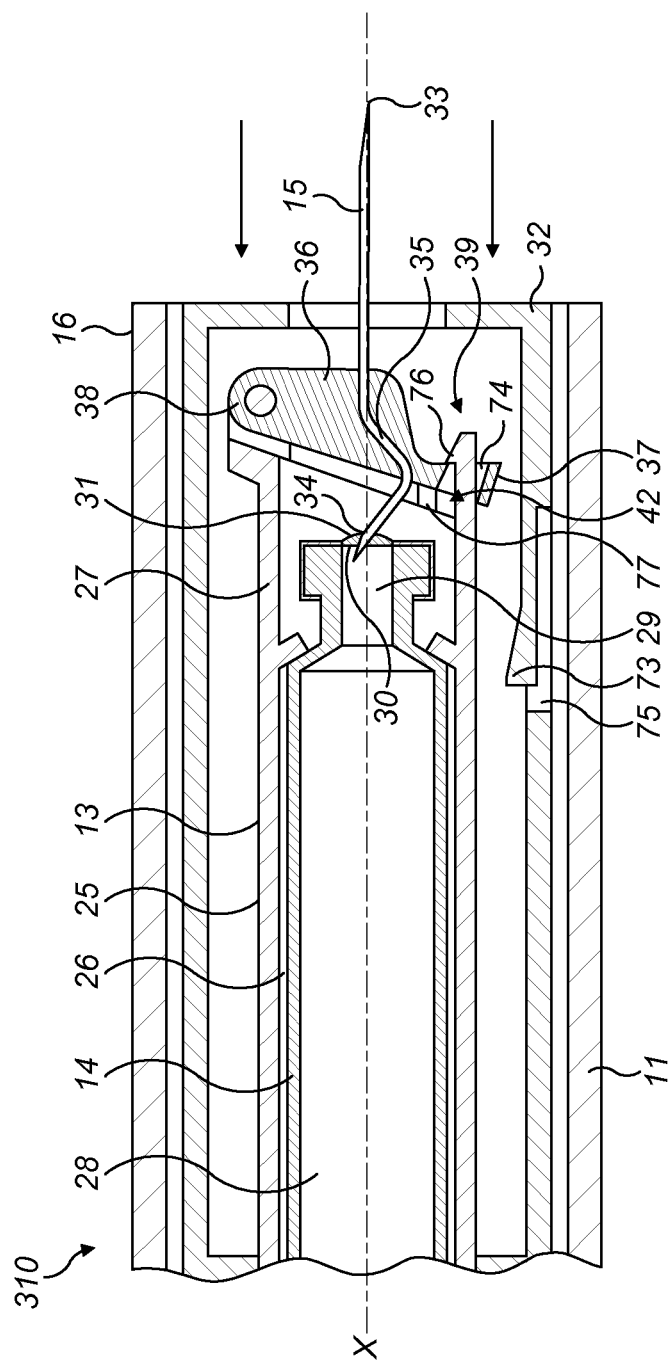

Initially, the sleeve 32 is in the deployed position so that the lug 73 is spaced from the needle holder 36 (FIG. 6A). In use of the device 310, a user pushes the sleeve 32 towards the retracted position to expose the needle 15. As the sleeve 32 slides towards the retracted position, the lug 73 engages the first end 37 of the needle holder 36 such that the needle holder 36 pivots from the storage position towards the use position (FIG. 6B). Simultaneously, the hook 76 engages in the opening 74 and snaps with the needle holder 36 to retain the needle holder 36 in the use position. The stop 77 stops the course of the needle 15 once the needle 15 has reached the use position (FIG. 6C). The device 110 is the ready for injection. Once the needle 15 is in the use position, the lug 73 is no longer in contact with the needle holder 36 so that the sleeve 32 can be further pushed within the housing 11 to reach the retracted position in which the needle 15 is then exposed to enable injection of medicament into the patient's body.

Figure 6D:
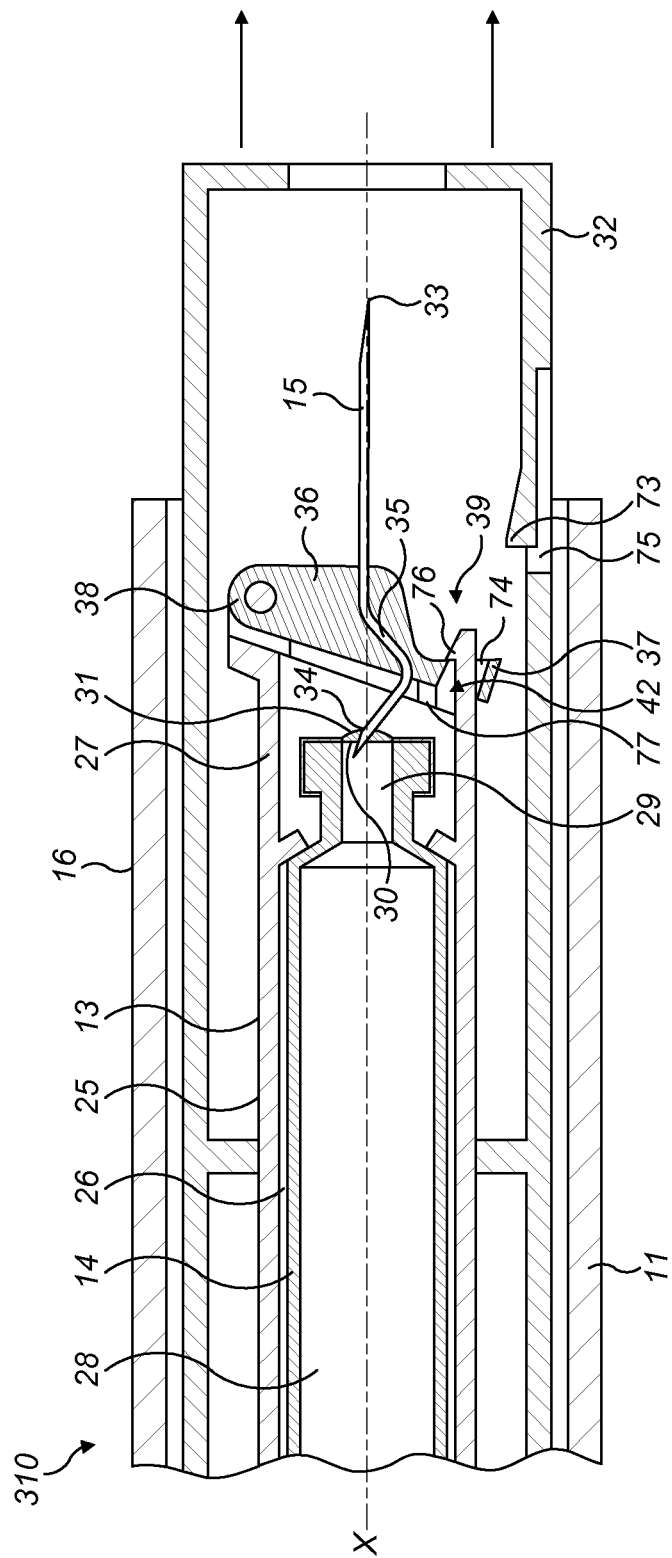

Once the injection has been performed, the needle 15 remains in the use position. The sleeve 32 is pushed back towards the deployed position by a spring (not shown) to prevent exposure of the needle 15 (FIG. 6D). As the sleeve 32 moves towards the deployed position, the lug 73 slides over the first end 37 needle holder 36.

It will be appreciated that various changes and modifications can be made to the medicament injection device described herein without departing from the scope of the present disclosure, as set out in the appended claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A medicament injection device, comprising:
a housing;
a cartridge holder mounted in the housing and configured to receive a cartridge containing a medicament;
an injection needle having a proximal end and a distal end;
an injection needle holder to which the injection needle is fixed; and
an actuating mechanism for pivoting the injection needle holder and the injection needle relative to the cartridge holder between a storage position in which the distal end of the injection needle is spaced from the cartridge when the cartridge is received in the cartridge holder and a use position in which the distal end of the injection needle can engage the cartridge when the cartridge is received in the cartridge holder,
wherein the actuating mechanism is configured such that actuation of the actuating mechanism causes pivoting movement of the injection needle from the storage position towards the use position.

2. The medicament injection device according to claim 1, wherein the injection needle holder is pivotally mounted to the cartridge holder.

3. The medicament injection device according to claim 1, further comprising a locking mechanism adapted to hold the injection needle in the use position.

4. The medicament injection device according to claim 3, wherein the locking mechanism includes a first locking element provided on the cartridge holder and a second locking element provided on the injection needle holder, wherein when the injection needle holder is in the use position, the first and second locking elements cooperate to prevent the injection needle from moving towards the storage position.

5. The medicament injection device according to claim 1, wherein the injection needle comprises a curved region between the distal end and the proximal end.

6. The medicament injection device according to claim 1, further comprising a cap for shielding the proximal end of the injection needle, the cap being detachably mounted to the housing.

7. The medicament injection device according to claim 6, wherein the actuating mechanism is configured such that pulling the cap away from the housing causes the injection needle to pivot from the storage position towards the use position.

8. The medicament injection device according to claim 7, wherein the actuating mechanism comprises a gear provided on the injection needle holder and a plurality of teeth disposed on the cap, the gear and the plurality of teeth cooperating so that pulling the cap away from the housing causes rotational movement of the gear and pivotal movement of the injection needle holder from the storage position towards the use position.

9. The medicament injection device according to claim 7, wherein the actuating mechanism comprises a first projection provided on the injection needle holder and a second projection provided on the cap, the first and second projections being configured such that pulling the cap away from the housing causes engagement of the second projection with the first projection and pivotal movement of the injection needle holder from the storage position towards the use position.

10. The medicament injection device according to claim 1, wherein the actuating mechanism comprises an actuator protruding through a sidewall of the housing and connected to the injection needle holder, wherein moving the actuator relative to the housing causes pivotal movement of the injection needle holder between the storage position and the use position.

11. The medicament injection device according to claim 10, wherein the actuator comprises a plurality of teeth and the injection needle holder comprises a gear, wherein the gear and the plurality of teeth are configured to cooperate so that sliding the actuator relative to the housing causes rotational movement of the gear and pivotal movement of the injection needle holder from the storage position towards the use position.

12. The medicament injection device according to claim 10, wherein the actuator comprises an arm integrally formed with the injection needle holder.

13. The medicament injection device according to claim 1, further comprising a retractable sleeve mounted in the housing and configured to slide along a longitudinal axis of the housing between a deployed position in which the sleeve protrudes from the housing and a retracted position in which the sleeve is retracted within the housing, wherein the actuating mechanism is configured such that pushing the sleeve towards the cartridge holder causes the injection needle holder to move from the storage position towards the use position.

14. The medicament injection device according to claim 13, wherein the sleeve comprises a lug configured to engage an end of the injection needle holder when the sleeve is pushed towards the retracted position such that the injection needle holder pivots from the storage position towards the use position.

15. The medicament injection device according to claim 1, further comprising the cartridge containing the medicament, the cartridge being received in the cartridge holder.

* * * * *

UNITED STATES PATENT AND TRADEMARK OFFICE
CERTIFICATE OF CORRECTION

PATENT NO. : 11,007,323 B2
APPLICATION NO. : 15/778252
DATED : May 18, 2021
INVENTOR(S) : Marc Schader, Michael Helmer and Peter Nober It is certified that error appears in the above-identified patent and that said Letters Patent is hereby corrected as shown below:

In the Specification

In Column 1, Line 10 (approx.), after "filed" delete "in"

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 11,007,323 B2
APPLICATION NO. : 15/778252
DATED : May 18, 2021
INVENTOR(S) : Schader et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 114 days.

Signed and Sealed this
Sixth Day of September, 2022

Katherine Kelly Vidal
*Director of the United States Patent and Trademark Office*